(12) United States Patent
Becker et al.

(10) Patent No.: US 6,774,613 B1
(45) Date of Patent: Aug. 10, 2004

(54) SEMICONDUCTOR GAS SENSOR, GAS SENSOR SYSTEM AND METHOD OF GAS ANALYSIS

(75) Inventors: Thomas Becker, Ottobrunn (DE); Stephan Muehlberger, Reit im Winki (DE); Gerhard Mueller, Grafing (DE)

(73) Assignee: EADS Deutschland GmbH, Munich (DE)

( * ) Notice: Subject to any disclaimer, the term of this patent is extended or adjusted under 35 U.S.C. 154(b) by 0 days.

(21) Appl. No.: 09/980,122
(22) PCT Filed: May 12, 2000
(86) PCT No.: PCT/DE00/01510

§ 371 (c)(1),
(2), (4) Date: Apr. 5, 2002

(87) PCT Pub. No.: WO00/73776

PCT Pub. Date: Jul. 12, 2000

(30) Foreign Application Priority Data

May 31, 1999 (DE) .......................................... 199 24 906

(51) Int. Cl.⁷ ............................................... G01N 27/00
(52) U.S. Cl. ..................................................... 324/71.5
(58) Field of Search ............................... 324/71.5, 459, 324/464, 691, 692, 693; 73/31.06, 31.05, 19.01, 23.2, 25.01

(56) References Cited

U.S. PATENT DOCUMENTS

| 4,455,378 A | 6/1984 | Heiland et al. |
| 5,811,662 A | 9/1998 | Williams et al. |

FOREIGN PATENT DOCUMENTS

| DE | 4139721 | 6/1993 |
| DE | 4243644 | 6/1994 |
| EP | 0 157 247 | 10/1985 |
| FR | 1019941 | 2/1953 |
| GB | 2218523 | 11/1989 |
| WO | WO 93/08467 | 4/1993 |

OTHER PUBLICATIONS

B. Ruhland, et al., "Gas–kinetic interactions of nitrous oxides with $SnO_2$ surfaces" Sensors and Actuators, B 50 (1998) pp. 85–94.
PCT Search Report w/Translation.

*Primary Examiner*—N. Le
*Assistant Examiner*—Amy He
(74) *Attorney, Agent, or Firm*—Crowell & Moring LLP (57) ABSTRACT

A semiconducting gas sensor includes a gas-sensitive layer, a heater for heating the layer to a defined measuring temperature, and contact electrodes for measuring the electrical resistance of the gas-sensitive layer enclosed within a microchamber, in which the gas-sensitive layer is arranged. The chamber can be sealed from the outside, and is constructed so that the chamber volume is small enough to allow at least one component of the gas or gas mixture that is to be analyzed to be at least largely exhausted via conversion on the gas-sensitive layer, within a predetermined measuring interval. With the limited gas store and the conversion of a component of the gas during the measurement process, gases or gas mixtures comprising several components can be analyzed. In this, the measuring signal is reexamined following the conversion of at least one component. Within the chamber, several sensor elements may be arranged with gas-sensitive layers, and may be operated at different temperatures. One gas sensor system, for example, is comprised of at least two semiconducting gas sensors having microchambers, which are arranged within a system of gas lines and valves, and can be filled individually.

26 Claims, 10 Drawing Sheets

SEMICONDUCTOR GAS SENSOR, GAS SENSOR SYSTEM AND METHOD OF GAS ANALYSIS

This application claims the priority of PCT International Application No. PCT/DE00/01510, filed 12 May 2000 and German patent document No. 199 24 906.7 filed 31 May 1999, the disclosure of which is expressly incorporated by reference herein.

The present invention relates to a semiconducting gas sensor in accordance with the preamble of Patent claim 1, a gas sensor system, and a method of gas analysis using a semiconducting gas sensor.

The present invention relates to a semiconducting gas sensor, and to a method of gas analysis using a semiconducting gas sensor, In some fields, gas analysis is of great importance. For example, in the combustion of fossil fuels, carbon monoxide and nitrous oxides or $NO_x$, are produced, which may then be converted to $O_3$. The damage to the environment caused by these substances is considerable. For this reason it is highly imperative that exhaust gases produced by internal combustion engines be analyzed, with an eye to reducing their emission of pollutants.

One possibility for gas analysis is presented by semiconducting gas sensors, in which a gas-sensitive metallic oxide layer, such as $SnO_2$, is brought to a specific measuring temperature. By measuring the electrical resistance of the gas-sensitive layer at a specific temperature, the gas concentrations, for example of CO, $NO_x$, or $O_3$, can be determined.

The article by B. Ruhland, et al., "Gas-Kinetic Interactions of Nitrous Oxides with $SnO_2$ Surfaces", Sensors and Actuators B 50 (1998) pp 85–94, discusses a semiconducting gas sensor of this type. In this known gas sensor, a thin layer of $SnO_2$ is placed on a heating structure. An $SiO_2$ layer separates a heating element from the gas-sensitive $SnO_2$ layer. The heating structure with the gas-sensitive layer is arranged on a $Si_3N_4$ membrane, which is then placed over a silicon substrate. In the measurement process, the gas that is to be analyzed flows over the sensor element. The bombardment with the gas components to be analyzed can also be accomplished via diffusion.

In the measurement of gases comprising several components, the problem arises that the effects of the individual gas components may become superimposed in the measuring signal. For example, at a measuring temperature of 400° C., a bombardment of the gas-sensitive layer with CO or NO leads to a reduction in the electrical resistance of the gas-sensitive layer, while a bombardment with $NO_2$ at this temperature results in an increase in electrical resistance. Furthermore, the contact between the gas-sensitive layer and ozone results in increased resistance. For this reason, the individual concentrations in the gas mixture frequently cannot be precisely determined.

One possibility for solving this problem consists in providing an arrangement comprising several sensors having different measuring temperatures. While a considerable degree of $NO_2$ sensitivity is present even at relatively low temperatures of 150° C. to 250° C., a suitable measuring temperature for CO, for example, lies between 350° C. and 450° C. The arrangement with the whole sensor array, however, is expensive, and thus associated with relatively high costs.

Another approach to solving the problem involves obtaining comparative sets of data for defined individual gases and gas mixtures at various temperatures via experimentation. To this end, the above-mentioned publication provides for a bombardment of several sensor elements with individual gas components at defined concentrations, in order to determine the behavior of electrical resistance, as a function of temperature. With the resistance behavior determined in this manner, it is then possible to analyze a gas mixture comprised, for example, of CO and $NO_2$ using two sensors, wherein one sensor is operated at 200° C. and one sensor is operated at 400° C. One disadvantage of this process is that it allows only very simple gas mixtures to be analyzed. Furthermore, interactions between the gases are not taken into account.

In addition, the high $O_3$ sensitivity disrupts the measurement process significantly. In many cases, the ozone sensitivity outweighs all other effects. For example, with ozone concentrations that are higher than 100 ppb the measuring signal can be interpreted only as an ozone signal.

It is thus one object of the present invention to create a semiconducting gas sensor and a gas sensor arrangement that is suitable for analyzing a gas or gas mixture comprising a number of components, such as, for example, ozone and that can be produced simply and cost-effectively. Furthermore, a method of gas analysis is to be provided, which will enable the analysis of a gas or gas mixture comprising a number of components via semiconducting sensors.

This and other objects and advantages are achieved by the semiconducting gas sensor according to the invention, which comprises a gas-sensitive layer, whose electrical conductivity can be altered via contact with a gas, a heating apparatus for heating the layer to a defined measuring temperature, contact electrodes for measuring the electrical resistance or the electrical conductivity of the gas-sensitive layer, and a chamber in which the gas sensitive layer is positioned. The chamber can be sealed from the outside; and the volume of the chamber is small enough that at least one component of the gas or gas mixture is largely exhausted via conversion, within a predetermined measuring interval, for example on the gas-sensitive layer.

In this manner, the disruptive effects of ozone on the measurement process can be eliminated.

With the small chamber volume, individual components of the gas become converted during the measuring process, so that they do not contribute, or contribute only slightly, to the measuring signal. The remaining measuring signal is then no longer superimposed by the effects of the gas components that have already been converted, allowing the concentrations of the remaining components to be more easily determined. With the invention it is possible to determine the concentrations of different gas components in a gas mixture, without requiring a multitude of sensors operating at different temperatures, which require costly evaluation. In addition, the gas analysis can be accomplished within a relatively short period of time, with the chamber volume being dependent upon the type of gas to be analyzed and the desired duration of the measuring interval.

Advantageously, the semiconducting gas sensor comprises a regulating device that enables the heating of the gas-sensitive layer in stages, thus allowing individual components of the gas mixture to be selectively converted at predetermined measuring temperatures. Preferably, the semiconducting gas sensor is produced using micromechanical technology, for example via Si technology. This enables a simple, cost-effective production, and a standard implementation of the sensor.

A platinum heating resistor, arranged in a meandering pattern, is preferably used as the heating device. The contact electrodes are preferably also made of platinum. This serves to produce increased temperature stability, while preventing mutual interference between the electrodes and the resistance material.

Advantageously, a passivating layer, comprised, for example, of $SiO_2$, is positioned between the heater and the gas-sensitive layer and serves as an insulator. Specifically, a silicon substrate may be provided as the supporting material, along with a nitride membrane, which separates the heater from the substrate.

The gas-sensitive layer is preferably comprised of $SnO_2$, however it can also be made of other metallic oxides such as $WO_3$ and titanium oxide, or of organic materials such as phthallocyanine.

The semiconducting gas sensor is preferably designed to be suitable for measuring concentrations of CO, $NO_2$, NO, and/or $O_3$. The chamber is preferably a microchamber made, for example, of silicon. The chamber volume advantageously measures approx. 10 to 500 $\mu l$, preferably 10 to 100 $\mu l$, and most preferably approx. 40 $\mu l$.

In accordance with a further aspect of the invention, a gas sensor system is provided, which comprises several semiconducting gas sensors as specified in the invention, along with an arrangement of regulated valves and lines for the inlet and outlet of gas. In this manner, it is possible to create redundancies, and to cost-effectively increase the lifespan of the system. In addition, a multitude of gas sensors may be used individually, allowing an improvement in measuring quality or precision to be achieved. Preferably, the semiconducting gas sensors are arranged in a parallel connection, wherein the valves may be controlled individually.

In accordance with a further aspect of the invention, a method of gas analysis using a semiconducting gas sensor is provided, which comprises the following steps: preparing a semiconducting gas sensor with a gas-sensitive layer in a sealable chamber; filling the chamber with a gas or gas mixture that is to be analyzed, and sealing the chamber; heating the gas-sensitive layer to a predetermined measuring temperature, and examining a measuring signal that is dependent, for example, upon the electrical conductivity or the ohmic resistance of the gas-sensitive layer, at a moment of measurement in which at least one gas component has been exhausted via conversion within the chamber so that it does not contribute, or contributes relatively slightly, to the measuring signal; and determining of the content of at least one remaining gas component from the remaining measuring signal.

With this process, gases or gas mixtures comprising several components, including ozone, may be easily analyzed, while the cost remains low, and the evaluation process implemented can be simple.

Advantageously, the measuring signal is used at least two different times during the measurement process to determine the components of the gas. For example, from the peak of the measuring signal and its subsequent decrease, the concentration of at least one component of the gas can be determined. Advantageously, the measuring temperature lies within a range of approx. 20° C. to 550° C., preferably within a range of approx. 50° C. to 400° C., and most preferably within a range of approx. 200° C. to 400° C. Therein, the heating process may be implemented gradually or in stages, with measurements being taken at different temperature stages. Most preferably, a semiconducting gas sensor as specified in the invention and/or a gas sensor system as specified in the invention are used in this process.

The invention will be described below by way of example using the attached figures, wherein.

DETAILED DESCRIPTION OF THE DRAWINGS

Figure 1:
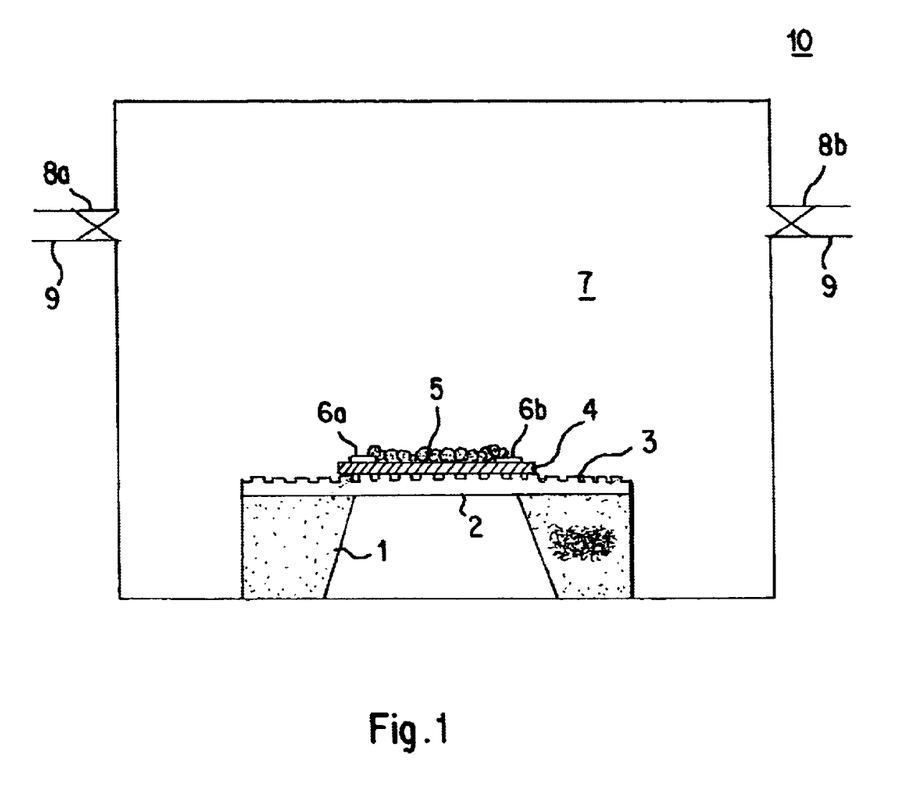
FIG. 1 shows a schematic illustration of a cross-section of a semiconducting gas sensor as specified in the invention.

FIG. 1 depicts a gas sensor 10 as specified in the invention. On a wafer or silicon substrate 1, which serves as the carrier, a nitride membrane 2 is positioned as a passivating layer. The nitride membrane 2 serves as an etch stop in the production of the wafer. On top of the membrane 2 is a heater 3 formed by a platinum heating resistor. The platinum heating resistor is arranged in a meandering pattern on top of the membrane 2, and is operated at a voltage of up to approx. 5 volts. The platinum heating resistor or heater 3 possesses a high level of temperature stability, hence the amount of sensor drift experienced is quite low. On top of the heater 3, a passivating layer 4 is positioned, which serves as an insulator and is made of $SiO_2$. This provides the advantage of a simple and precise method of production, which is also cost-effective. On top of the passivating layer 4 is the gas-sensitive layer 5 made of $SnO_2$. Contact electrodes 6a and 6b are also arranged on the passivating layer 4, for the purpose of determining the electrical resistance of the gas-sensitive layer 5. The sensor element constructed in this manner is positioned within a chamber 7, which can be sealed from the outside via valves 8a and 8b. The chamber 7 is small enough that gas components are converted within the chamber during the measuring process, and, after a predetermined measuring interval, no longer contribute to the measuring signal, or contribute only insignificantly.

In the present case, the chamber 7 is designed as a microchamber, wherein the chamber volume is approx. 0.5 $cm^3$. Depending upon the purpose of the measurement or upon the gas to be analyzed, substantially smaller chamber volumes are also possible, for example within the range of approx. 0.05 $cm^3$. Chambers this small can be produced very effectively using microtechnology. During the measuring process, so-called "no flow" conditions prevail within the chamber, in other words only a limited store of individual gases is present, which are at least partially converted. Via the valves 8a, b and gas lines 9, the chamber 7 can be filled, and sealed from the outside when measurement begins. This serves to prevent any subsequent diffusion of gas components, such as may occur, for example, with macroscopic gas volumes. The chamber 7 may also possess a larger volume of up to a few 100 $\mu l$. However, a volume that is between 10 and 100 $\mu l$ is especially advantageous. In the preferred embodiment, the chamber is made of silicon.

Since the volume of the chamber is dependent upon the specific measuring purpose, the size of the chamber 7 must be designed and constructed accordingly. For example, the volume of the chamber 7 must be designed such that the gas will be allowed to diffuse over a predetermined measuring interval from the most remote point of the chamber to the sensor element or to the gas-sensitive layer 5. The conversion of at least one gas component then follows, so that the store of gas becomes exhausted or converted in terms of this at least one component, within the desired measuring interval. It is not necessary, however, for a complete conversion to take place; rather, it is sufficient for these components to no longer contribute significantly to the measuring signal at a specific point in time, or for these components to no longer disrupt the signal. In other words, the conversion must proceed for as long during the predetermined measuring interval that the concentrations of the remaining components can be precisely determined.

In the embodiment illustrated here, the gas-sensitive layer 5 is comprised of stannic oxide pellets, in other words, a polycrystalline semiconducting material is present. Between the stannic oxide pellets are potential barriers, which are modulated via bombardment with gases. For example, when the surface of the stannic oxide pellets is bombarded with air, a surface coating with oxygen is produced, which is temperature dependent. The physisorbed or chemisorbed oxygen causes a depletion surface layer to form on the stannic oxide pellets at increasing temperatures, in other words a potential barrier is formed between the individual crystallites. This causes the level of electrical conductivity to fall.

Figure 2A:
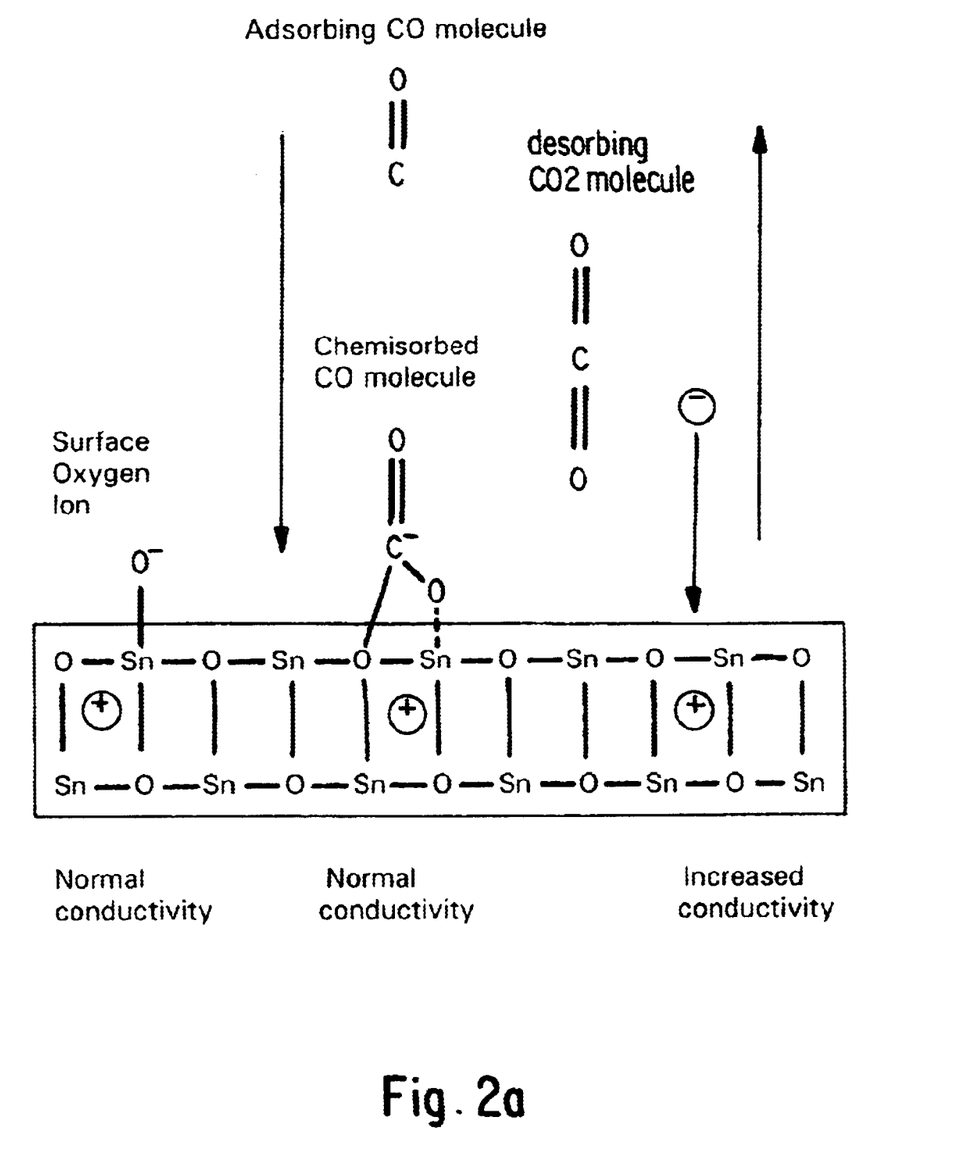
FIGS. 2a and b depict the reaction mechanisms for CO and NO on the gas-sensitive layer at 400° C.

In FIG. 2a, the reaction mechanism for CO on the gas-sensitive layer 5 is shown, based upon current knowledge. In this, a CO molecule is adsorbed on the surface, where it reacts with a surface oxygen ion, forming a $CO_2$ molecule and an electron:

$$CO_{gas} + O^-_{surface} \rightarrow CO_{2gas} + e^-$$

The $CO_2$ that is formed desorbs from the $SnO_2$ surface, and the electron is donated to the $SnO_2$. This causes an increase in the conductivity of the $SnO_2$ layer, that is, its electrical resistance drops. In other words, the depletion surface layer becomes smaller and the potential barrier is reduced. In this measurement process, a temperature of around 400° C. is advantageous, since the sensitivity level is relatively-high.

Figure 2B:
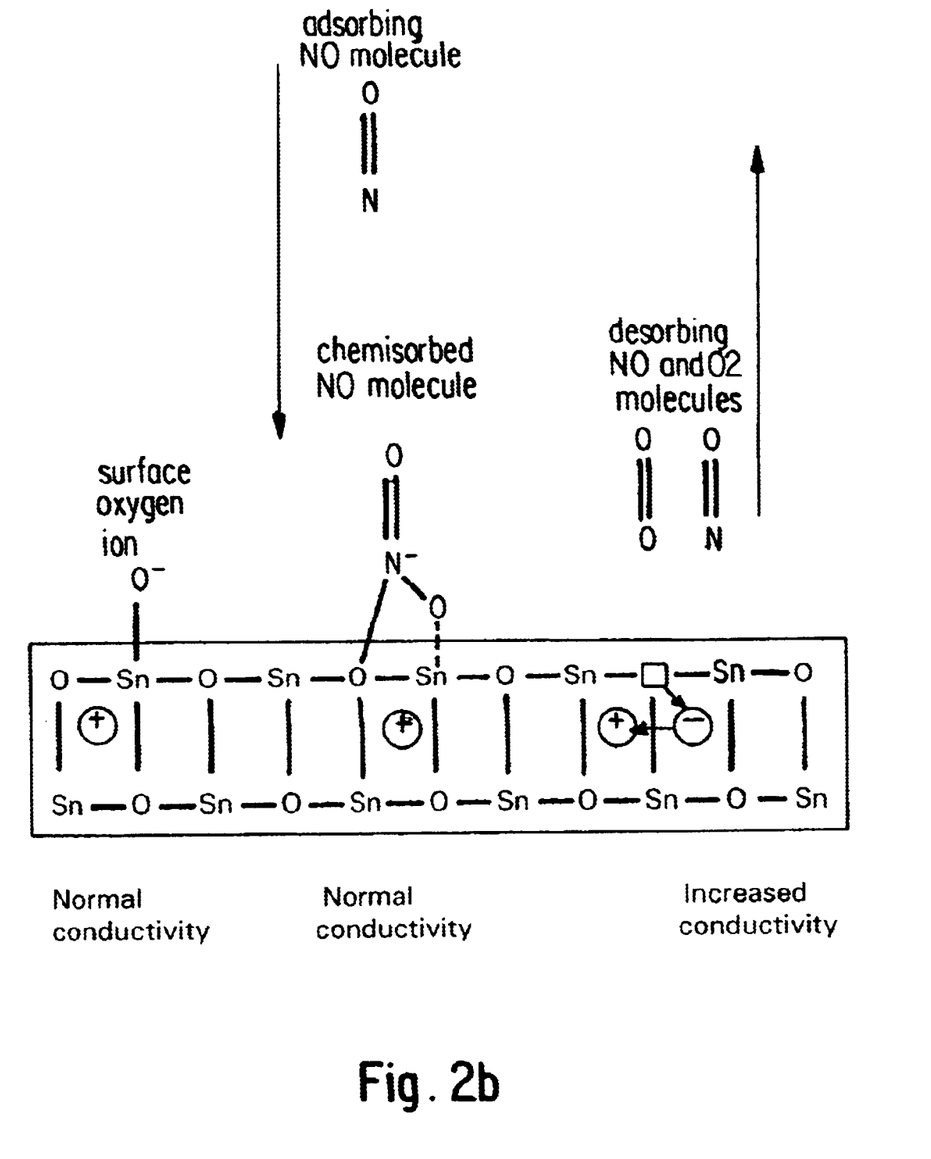

In FIG. 2b, the reaction mechanism for an NO molecule is depicted as an example. Obviously, the reaction mechanism for NO on the $SnO_2$ layer is very similar to the reaction mechanism for CO. With an oxygen ion $O^-$ on the surface of the gas-sensitive layer, an NO molecule is adsorbed or chemisorbed, producing the following reaction:

$$NO_{gas} + O^-_{surface} \rightarrow NO_{2gas} + e^-$$

NO and $O_2$ molecules are desorbed on the surface, and the electrical conductivity is increased. In this measurement process as well, the preferred temperature range is between 400° C. and 500° C.

Figure 3A:
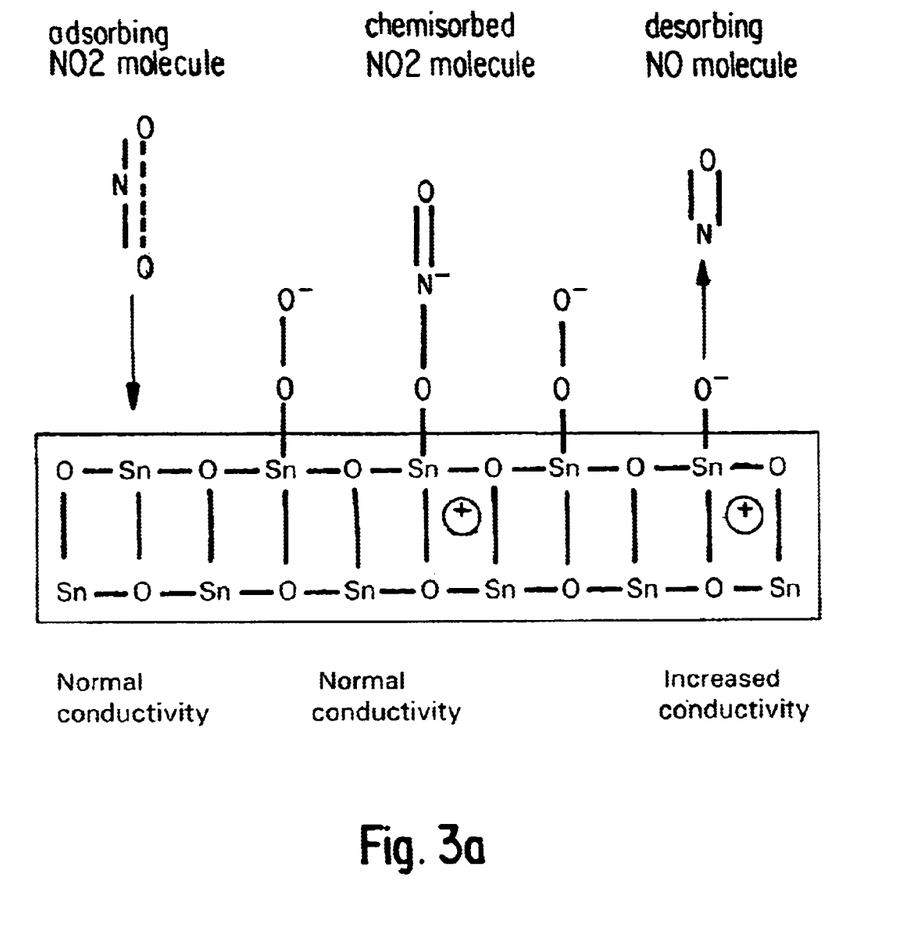
FIGS. 3a, b, and c depict various reaction mechanisms for $NO_2$ at a temperature of 200° C. or 400° C.

In the case of $NO_2$, a substantially more complex reaction process takes place. FIG. 3a shows the reaction mechanism for $NO_2$ on the gas-sensitive layer 5, at a temperature of up to 200° C. In this, an $NO_2$ molecule is adsorbed on the surface of the $SnO_2$ layer 5, and the following binds to the surface, gaining an electron:

$$NO_{2gas} + e^- \rightarrow NO^-_{2surface}$$

This causes the potential barriers on the $SnO_2$ grain boundaries to be increased, and the electrical conductivity to decrease. An NO molecule is then desorbed from the surface, and an $O^-$ is returned to the surface:

$$NO^-_{2surface} \rightarrow NO_{gas} + O^-_{surface}$$

Figure 3B:
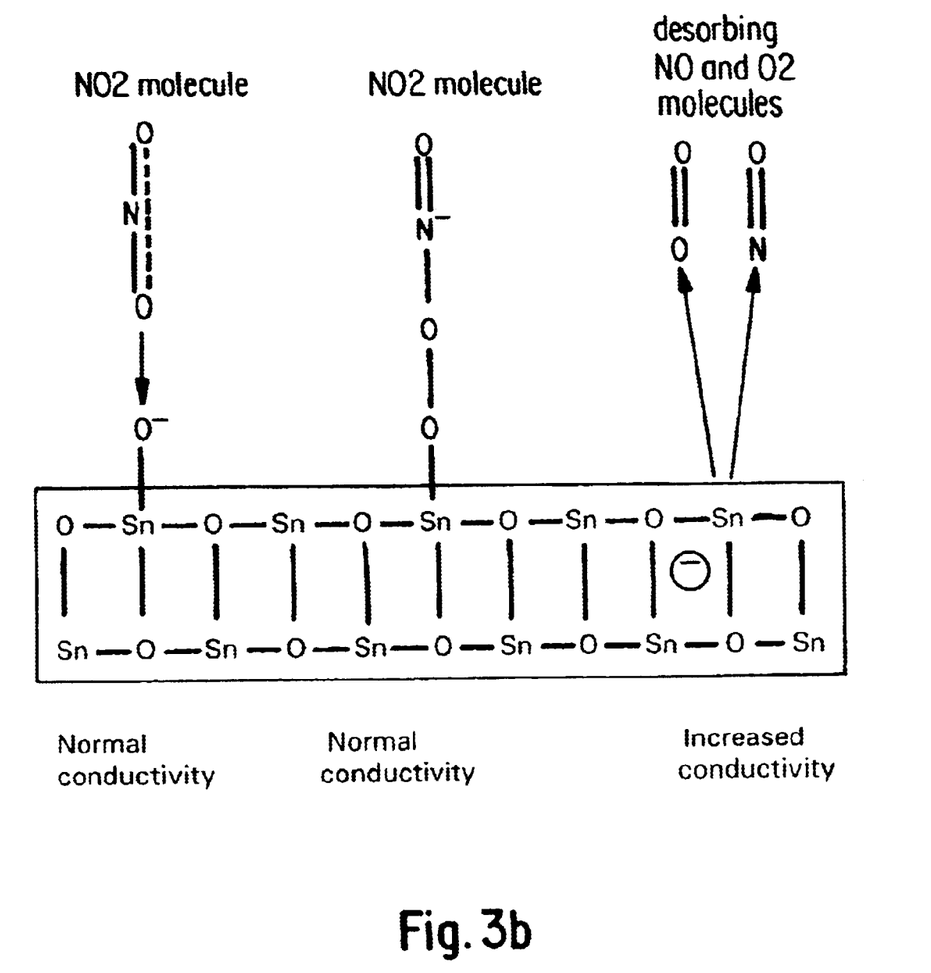

At a higher temperature of ca. 400° C., a concentration-dependent reaction takes place. The reaction mechanism for $NO_2$ at a temperature of 400° C. and at lower concentrations is depicted in FIG. 3b. The $NO_2$ molecule binds to the $O^-$ that is now present on the surface, after which NO and $O_2$ molecules are desorbed. In this, an electron is donated to the $SnO_2$ layer, causing the electrical conductivity to increase:

$$NO_{2gas} + O^-_{surface} \rightarrow NO_{gas} + O_{2gas} + e^-$$

Figure 3C:
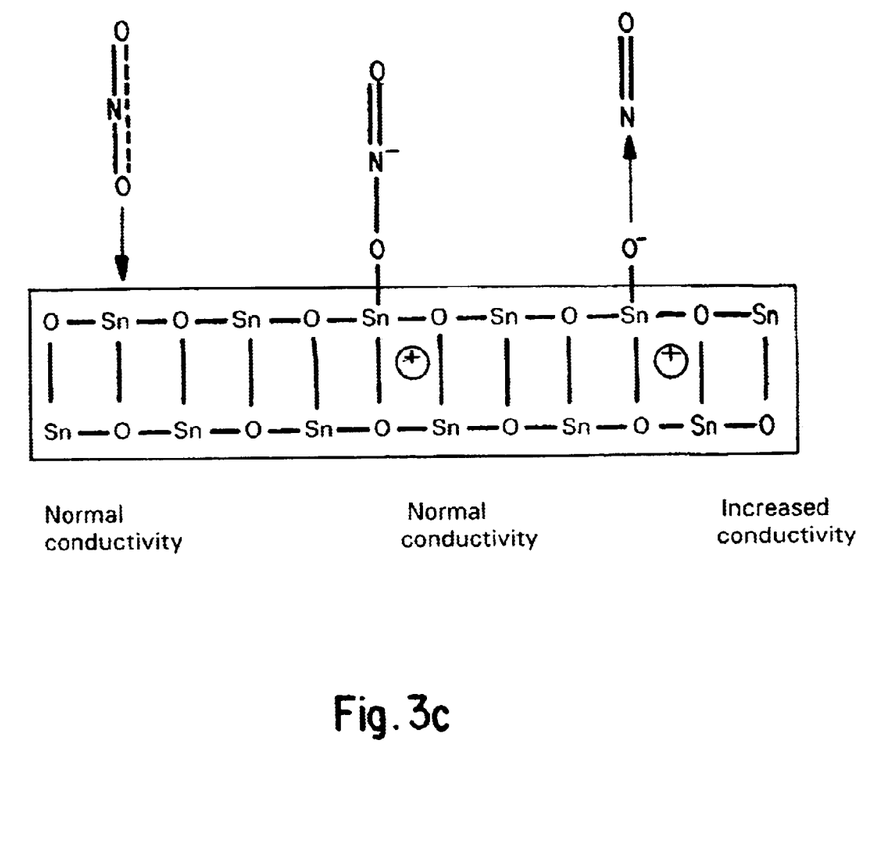

At higher concentrations, however, the reaction is different. FIG. 3c depicts the reaction mechanism for $NO_2$ on the $SnO_2$ surface at higher concentrations and at a temperature of 400° C. In this, $NO_2$ molecules are adsorbed, causing an electron to be acquired. NO then desorbs from the surface, and an $O^-$ is returned to the surface. The electrical conductivity is reduced:

$$NO_{2gas} + e^- \rightarrow NO_{gas} + O^-_{surface}$$

Furthermore, $O_3$ produces a strong effect on the measurement process, which influences the measuring signal substantially. Therein, an $O^-$ is bound to the surface of the gas-sensitive layer 5, and an $O_2$ molecule is desorbed from the surface. This reaction occurs primarily along the edges of the gas-sensitive layer 5, or in the case of thin layers. With thicker layers, however, the deeper areas remain unaffected by $O_3$. In contrast, other molecules, such as CO, penetrate to deeper areas where they react with the gas-sensitive layer 5 or with the $SnO_2$.

With the microchamber 7, the gas store within the chamber is limited. Via diffusion or flow, the $O_3$ molecules present in the chamber 7 eventually reach the surface of the gas-sensitive layer 5, where they are converted to $O_2$.

Of particular importance here is that residual $O_2$ molecules will not disrupt the measurement, since the sensor element with the gas-sensitive layer 5 will not react to the few $O_2$ molecules present.

Below, measurements conducted on various gases will be described.

Figure 4:
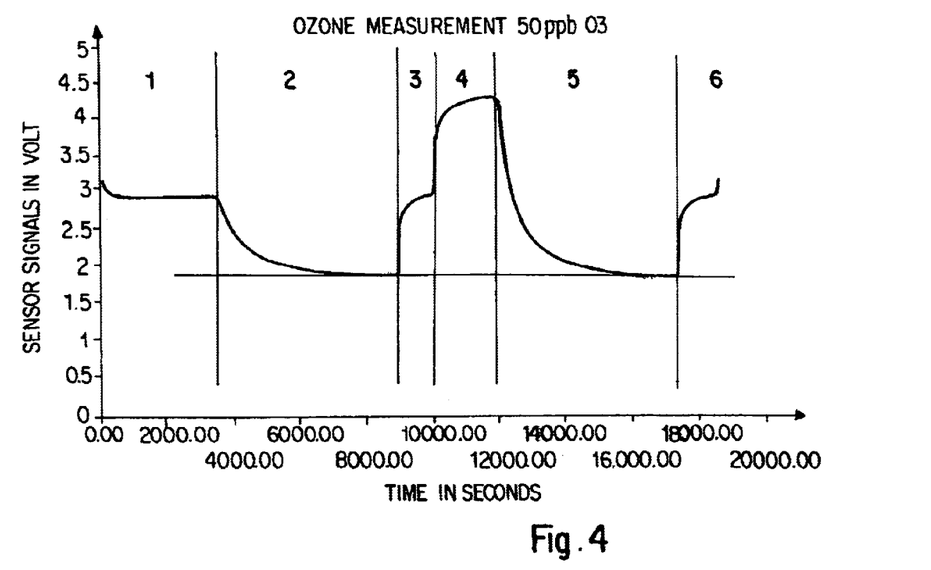
FIG. 4 depicts the sensor signal for an ozone measurement.

FIG. 4 depicts the sensor signal as a function of time in an ozone measurement. First, the valves 8a, 8b of the chamber 7 (FIG. 1) are opened, in order to achieve a constant flow of gas within the chamber. This allows the sensor to be conditioned. The gas flow is comprised of synthetic air with 30% relative humidity. This state is illustrated in FIG. 4 by the area 1. Therein, the sensor is at equilibrium with the surrounding, flowing air. The valves 8a, 8b are then closed, causing the humidity within the chamber to rise as a result of the heating of the chamber, as water desorbs from the chamber walls. The sensor signal drops and the final value is stored in a memory device as a calibration or zero gas value (area 2). The humidity reduces the electrical resistance of the $SnO_2$ layer, since the water on the $SnO_2$ layer forms $OH^-$ groups, wherein atomic hydrogen is released, resulting in a reduction of the $SnO_2$ layer.

In area 3 of FIG. 4, the valves 8a, 8b are reopened, causing the sensor to be reconditioned in the gas flow. The air humidity drops, and the measuring signal rises. In this area, the original conditions are reproduced. The area 4 depicts the addition of ozone (50 ppb) to the gas flow.

Now, the valves 8a, 8b are again closed (area 5). The actual measurement is conducted. In the chamber 7 a no-flow situation prevails, and the humidity within the chamber increases due to the heating of the chamber, as a desorption of $H_2O$ from the chamber walls takes place. The sensor signal drops, and the ozone in the chamber breaks down to $O_2$. This slight increase in $O_2$ concentration is not recognized by the sensor. Thus the sensor signal S in the area 5 achieves the same final value as in area 2. Then, in area 6, the valves are reopened, the original conditions are reproduced. What is decisive in this measurement process is that the sensor no longer recognizes the $O_3$ after a certain period of time, which is a function of the chamber volume and the concentration of $O_3$. Hence, the measuring signal is no longer affected by the $O_3$ after a certain period of time.

Figure 5:
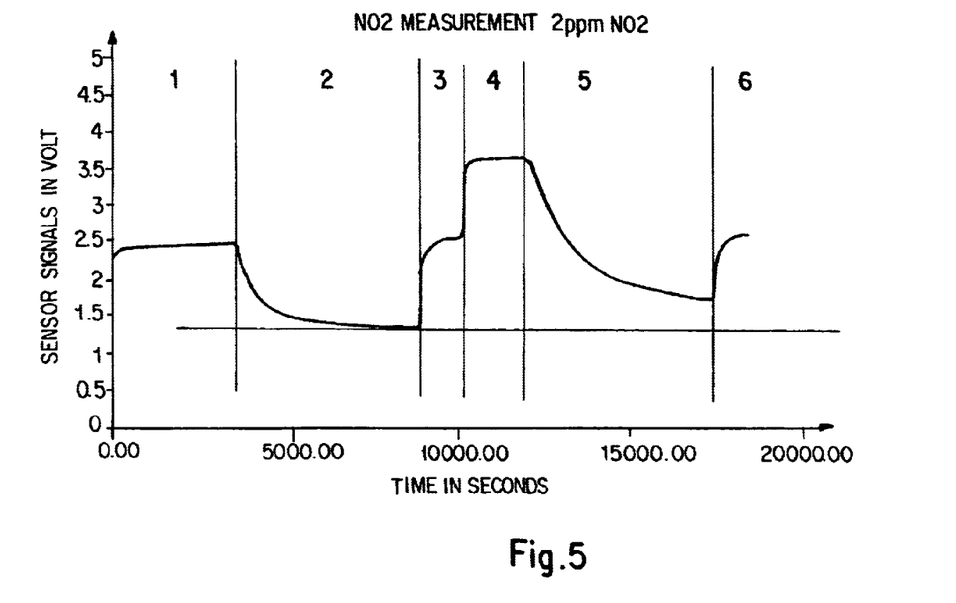
FIG. 5 depicts the sensor signal for an $NO_2$ measurement.

FIG. 5 depicts an $NO_2$ measurement. In comparison with an $O_3$ measurement, which is depicted in FIG. 4, here the sensor signal does not drop back down to the original value in area 5. Here, $NO_2$ desorbs as NO and $O_2$ from the stannic oxide surface, which is oxidized to a higher valency in the sealed measuring chamber 7, back to $NO_2$, since the chemical equilibrium at near room temperature is $NO_2$ or $N_2O_4$. The magnitude of the offset in area 5 is a measurement of the $NO_2$ concentration in the sealed measurement chamber 7.

The ozone concentration or the $NO_2$ concentration is determined by adjusting a function to fit the measuring signal, and comparing this with values in a reference table. The measuring signal follows an e function of the form $S=A+B\times EXP(t/tau)$. If this function is adjusted to fit the measuring signal, then the end value that will be established after an infinitely long period of time is obtained. The signal value obtained in this manner is assigned to an ozone concentration using a reference table.

With the $NO_2$ measurement in FIG. 5, the reference value from area 2 is derived from the calculated final value from area 5. This value is then also assigned an $NO_2$ concentration using a reference table.

Figure 6:
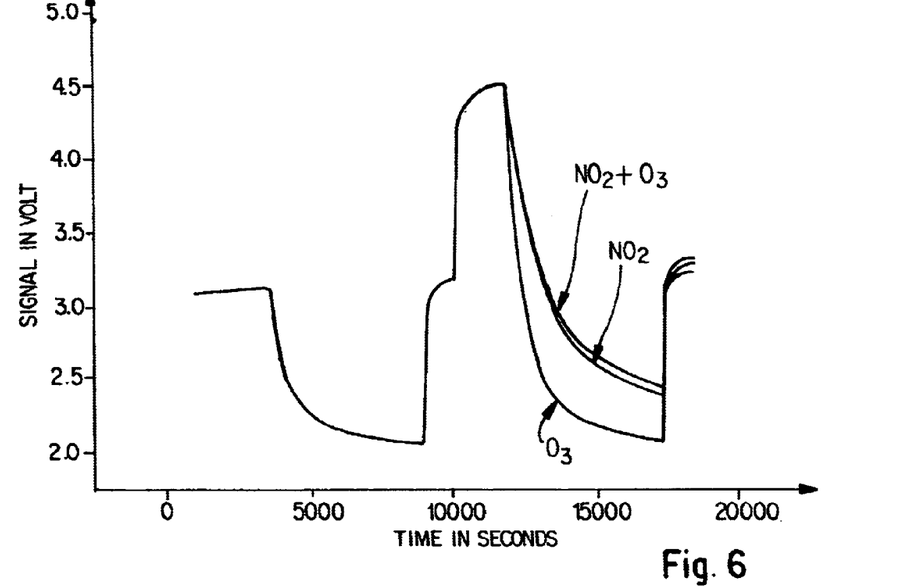
FIG. 6 depicts the sensor signal for both a pure $NO_2$ measurement, and a measurement of $O_3$, also in a gas mixture of $NO_2$ and $O_3$.

FIG. 6 depicts the measuring signal for both a pure $NO_2$ measurement and an $O_3$ measurement, as well as a measurement conducted using a gas mixture comprised of $NO_2$ and $O_3$. Herein, it is clear that with the combined addition of $NO_2$ and $O_3$ the sensor signal follows the course of the $NO_2$ measurement. Hence it follows that the percentage of $NO_2$ can be determined from the mixed signal in the no-flow situation. From the composite signal in the flow situation, with a low $NO_2$ concentration, the ozone concentration can be deduced directly, since the response of the sensor to ozone is much greater than its response to $NO_2$. With higher $NO_2$ concentrations, the ozone concentration is calculated using the measured $NO_2$ concentration.

Figure 7:
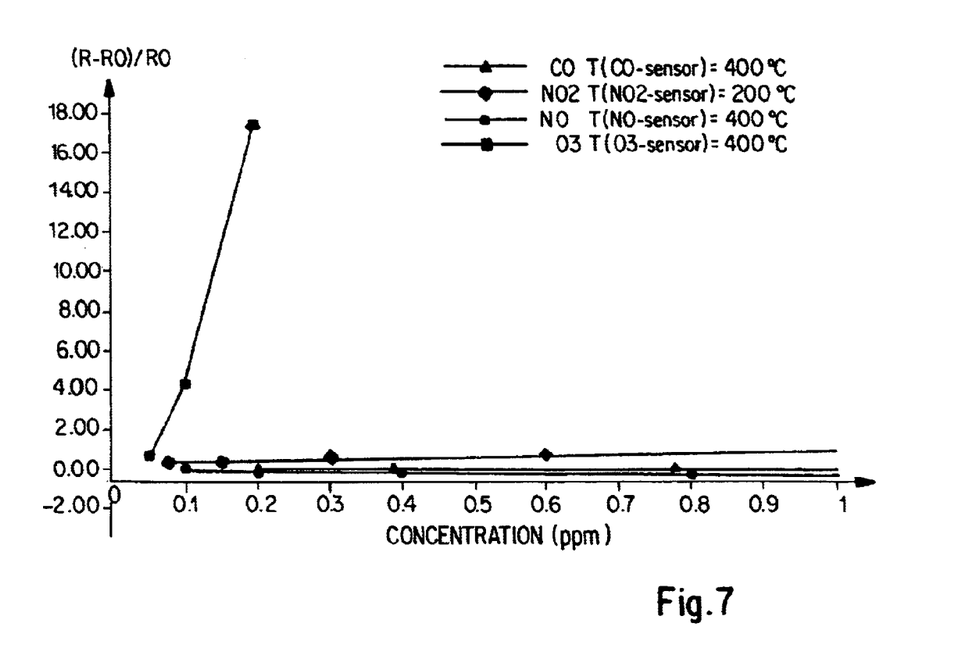
FIG. 7 depicts the sensor sensitivity as a function of the concentrations of various gases.

FIG. 7 depicts the sensor sensitivity as a function of the concentrations of various gases. Herein, it is clear that the sensitivity to ozone outweighs the sensitivity to all other gases. For signal evaluation this means that two cases must be differentiated. With ozone concentrations that are greater than 100 ppb, the measuring signal can be interpreted directly as an ozone signal. However, for concentrations that are below 100 ppb, the ozone signal must be corrected by the $NO_2$ component, as this gas produces the next highest effect on the sensor. The correction is made using the $NO_2$ value that is obtained via the no-flow measurement.

Gases like CO and $CH_4$ can be completely converted to $CO_2$ and $H_2O$. Therein, $CO_2$ produces no effect on the measuring signal, and the resulting quantity of $H_2O$ at low $CH_4$ concentrations is too small to produce an effect on the measuring signal. If, during the measurement process, gases should appear that have not been tested, but that could distort the measurement results, suitable filters are selected, such as are customarily used in gas-sensor technology, and are known to experts in the field.

Figure 8:
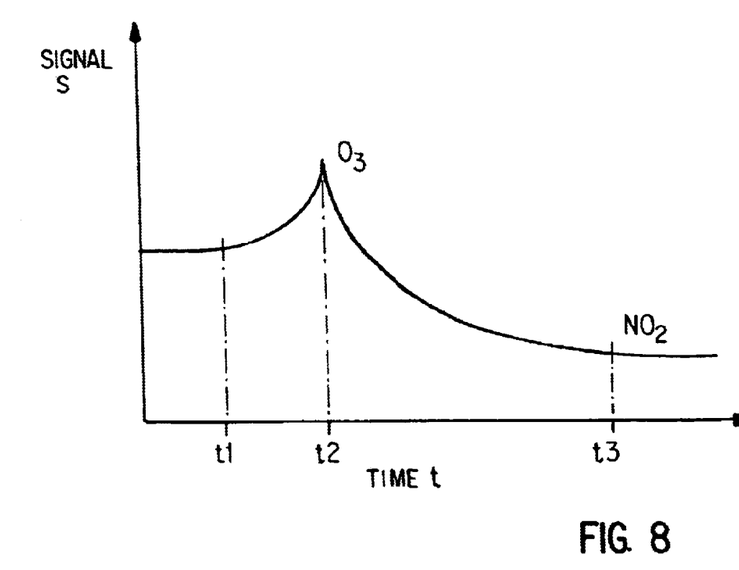
FIG. 8 depicts the measuring signal for a gas in which nitrous oxide and $O_3$ molecules are present.

The example illustrated in FIG. 8 shows a measurement of a gas in which nitrous oxide and $O_3$ molecules are present. By opening the valves 8a, 8b, the measuring chamber 7 is filled via the gas lines 9 with the gas that is to be analyzed.

With the heater 3, the gas-sensitive layer 5 is brought to a predetermined measuring temperature, or is held at this temperature if it has already been heated. The measuring temperature in this case is 400° C. The electrical resistance of the gas-sensitive layer 5 is measured via the contact electrodes 6a, 6b.

FIG. 8 shows the measuring signal S as a function of time t. At the start of the measurement, the signal S remains nearly constant, but increases sharply at time t1, and reaches a maximum level at time t2. This is followed by a relatively rapid drop in the signal S, and at time t3 it reaches a nearly constant value. At the start of the measurement, the measuring signal is determined mainly by the amount of $O_3$ present, in other words the effects of the nitrous oxide are completely masked. The sharp increase of the signal S up to time t2 is based upon the above-described reaction of the $O_3$ molecules on the $SnO_2$ surface. However, because the store of $O_3$ molecules in the chamber 7 is limited, and the $O_3$ molecules are eventually converted, a reduction of the measuring signal or the ohmic resistance in the $SnO_2$ layer now occurs, that is, after time t2. At time t3, the signal is then completely or almost entirely unaffected by $O_3$, and the signal value S at time t3 is characterized substantially by the concentration of the nitrous oxide or NO that is present. From this, the concentration of the nitrous oxide in the gas mixture can be determined, without influence by $O_3$.

Depending upon the purpose of the measurement or upon the established requirements, several sensor elements may also be arranged with gas-sensitive layers 5 in the chamber 7. These can, for example, be operated at different measuring temperatures, so that in the above-described manner the measurement of different gas components at time t3 can be determined. It is also possible to determine the concentration of different gas components via comparison with measured values at known concentrations. Herein, the measured value is applied at a time in which the $O_3$ components, or at least one component, has been completely or nearly completely converted, so that the remaining measuring signal characterizes the concentrations of the remaining components.

Figure 9:
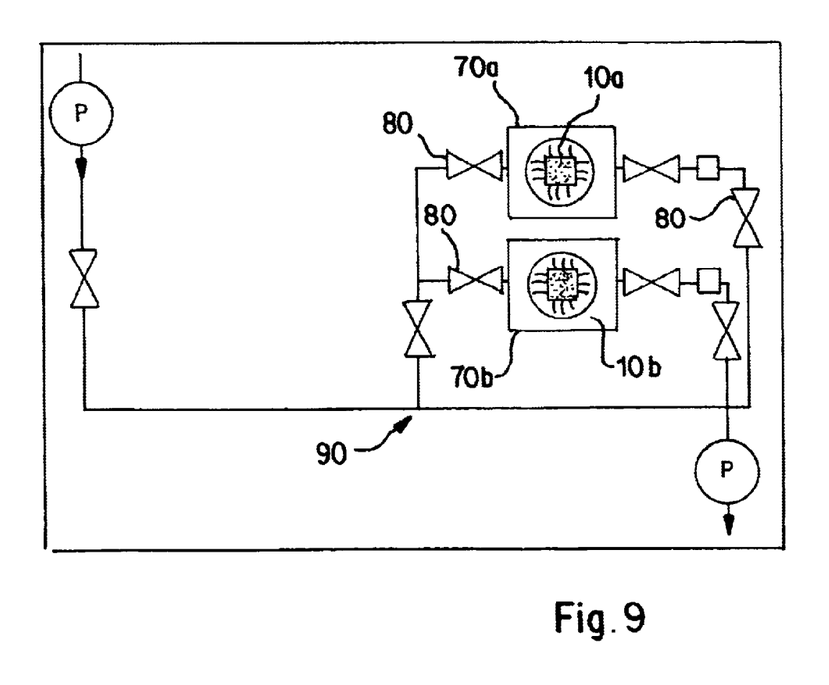
FIG. 9 shows an illustration in principle of the gas sensor system specified in the invention.

FIG. 9 depicts a preferred embodiment of a gas sensor system in accordance with the present invention. Herein, two semiconducting gas sensors 10a, 10b are arranged parallel to one another within a system of gas lines 90. The semiconducting gas sensors 10a, 10b were described above. Via regulated valves 80, the measuring chambers 70a, 70b of the semiconducting gas sensors 10a, 10b may be filled. The chambers 70a, 70b can be filled with gas and sealed individually based upon requirements or upon the intended measurement.

Figure 10:
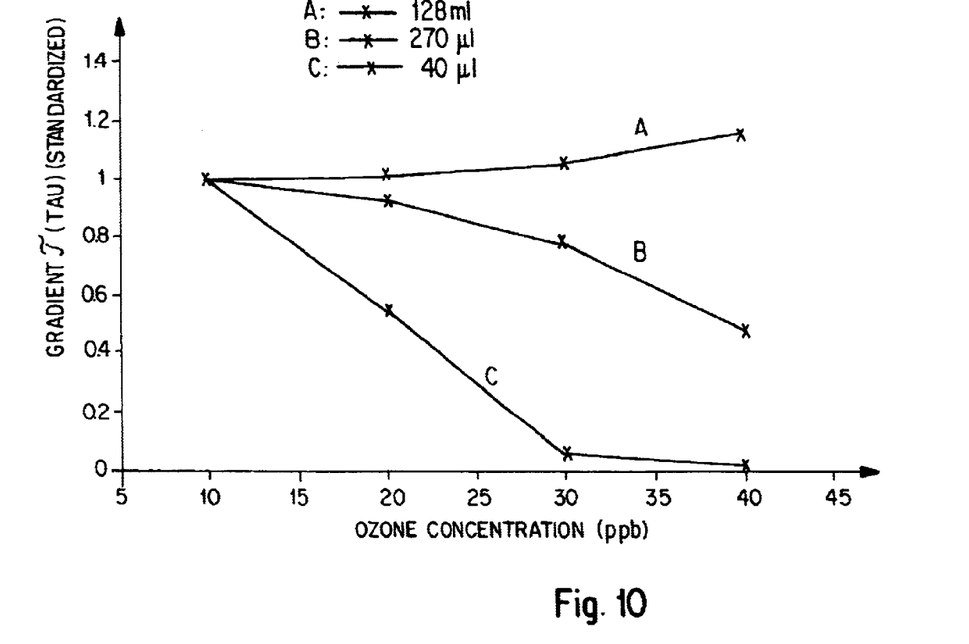
FIG. 10 depicts the conversion rate of ozone under no-flow conditions as a function of various ozone concentrations.

FIG. 10 depicts the conversion rate of ozone under no-flow conditions as a function of various ozone concentrations. Recorded here is the reaction rate, expressed via the gradient of the measuring curve, against various ozone concentrations. In a large measuring chamber, no conversion of ozone takes place within a reasonable interval of time. A small chamber size results in ozone conversion, and a further reduction of the volume increases the conversion rate.

In order to minimize the dead volume within the chamber 7 or the chambers 70a, 70b, flange-type valves are used. The gas flow system in the preferred embodiments is made of polyether etherketone (PEEK). This material is especially resistant to the gases described here. The gas flow system is implemented via specially designed bores in a plate or in a carrier material, which serves to further minimize the dead volume. The particular advantages of this design are the small chamber volume and the possibility of a measurement conducted in a no-flow situation within a particularly small chamber volume. By producing the chamber from silicon using micromechanical technology, the volume can be made extremely small, enabling simple methods of production and maintenance, and resulting in a considerable decrease in cost.

What is claimed is:

1. Semiconducting gas sensor comprising:
   a gas-sensitive layer whose electrical conductivity can be varied by contact with a gas;
   a heater for heating the layer to a predefined measuring temperature;
   contact electrodes for measuring the electrical resistance or the conductivity of the gas-sensitive layer; and
   a chamber in which the gas-sensitive layer is arranged; wherein,
   a valve arrangement is provided to seal the chamber from the outside and keep it closed during the measurement process, whereby during measurement a limited supply of individual gases in the chamber is at least partially converted; and
   volume of the chamber is such that at least one component of a limited gas store within the chamber is substantially exhausted via conversion within a predetermined measuring interval.

2. The semiconducting gas sensor in accordance with claim 1, further comprising a device for regulating heating of the gas-sensitive layer in stages whereby individual components of the gas can be selectively converted at predetermined measuring temperatures.

3. The semiconducting gas sensor in accordance with claim 1, wherein the gas sensor is produced using micromechanical technology.

4. The semiconducting gas sensor in accordance with claim 1, wherein the heater is a platinum heating resistor which is arranged in a meandering pattern.

5. The semiconducting gas sensor in accordance with claim 1, further comprising a passivating layer that is positioned between the heater and the gas-sensitive layer, and is made of $SiO_2$.

6. The semiconducting gas sensor in accordance with claim 1, wherein the contact electrodes are made of platinum.

7. The semiconducting gas sensor in accordance with claim 1, further comprising a silicon substrate as a carrier, and a nitride membrane, which separates the heater from the carrier.

8. The semiconducting gas sensor in accordance with claim 1, wherein the gas-sensitive layer is made of a material selected from the group consisting of $SnO_2$, $WO_3$, titanium oxide, and organic materials.

9. The semiconducting gas sensor in accordance with claim 8, wherein the organic materials comprise phthallocyanine.

10. The semiconducting gas sensor in accordance with claim 1, wherein the gas sensor is configured for measuring concentrations of CO, $NO_2$, NO, and/or $O_3$.

11. The semiconducting gas sensor in accordance with claim 1, wherein the chamber is made of silicon.

12. The semiconducting gas sensor in accordance with claim 1, wherein the chamber volume measures no more than 0.05 to 10 $cm^3$.

13. The semiconducting gas sensor in accordance with claim 1, wherein the chamber volume measures no more than 0.03 to 0.7 $cm^3$.

14. The semiconducting gas sensor in accordance with claim 1, wherein the chamber volume measures no more than 0.5 $cm^3$.

15. A gas sensor system comprising:
    a plurality of semiconducting gas sensors in accordance with claim 1; and
    lines for the inlet and outlet of gas via a valve arrangement of controllable valves.

16. The gas sensor system in accordance with claim 15, wherein the semiconducting gas sensors are arranged in a parallel connection.

17. The gas sensor system in accordance with claim 15, wherein the valves are controllable individually.

18. A method of gas analysis using a semiconducting gas sensor, comprising:
    providing a semiconducting gas sensor with a gas-sensitive layer;
    placing said gas sensor in contact with a gas or gas mixture that is to be analyzed;
    heating the gas-sensitive layer; and
    analyzing a measuring signal that is a function of the electrical conductivity of the gas-sensitive layer; wherein,
    the semiconducting gas sensor is provided in a sealable chamber;
    the chamber is filled with the gas or gas mixture that is to be analyzed, and is sealed;
    the gas-sensitive layer is held at a predetermined measuring temperature;
    the measuring signal is examined when at lest one component of the gas has been exhausted via conversion within the chamber, to a point at which it no longer supplies any significant contribution to the measuring signal; and
    a content of at least one remaining gas component is determined from the remaining measuring signal.

19. The method in accordance with claim 18, wherein:
    the measuring signal is examined as a function of time; and
    the measurement is used at least two different times to determine the gas components.

20. The method in accordance with claim 18, wherein the concentration of at least one gas component is determined from a maximum peak of the measuring signal and a subsequent drop thereof.

21. The method in accordance with claim 18, wherein the measuring temperature lies within a range of 20° C. to 550° C.

22. The method in accordance with claim 18, wherein the measuring temperature lies within a range of 50° C. to 400° C.

23. The method in accordance with claim 18, wherein the measuring temperature lies within a range of approximately 200° C. and 400° C.

24. The method in accordance with claim 18, wherein:
    heating is gradual; and
    measurements are taken at different measuring temperatures.

25. The method in accordance with claim 18, wherein said gas sensor comprising a gas sensor according to claim 1.

26. The method in accordance with claim 18, wherein said gas sensor comprises a gas sensor system according to claim 16.

* * * * *